United States Patent [19]

Tanimoto et al.

[11] Patent Number: 4,620,038
[45] Date of Patent: Oct. 28, 1986

[54] PROCESS FOR PRODUCING METHYL ETHYL KETONE

[75] Inventors: Hirotoshi Tanimoto; Mutsuo Yamada; Yoshijiro Arikawa; Taiji Kamiguchi; Yasuyuki Nishimura; Hiroyuki Kaku, all of Kure, Japan

[73] Assignee: Babcock-Hitachi Kabushiki Kaisha, Tokyo, Japan

[21] Appl. No.: 706,263

[22] Filed: Feb. 27, 1985

[30] Foreign Application Priority Data

Feb. 29, 1984 [JP] Japan ................. 59-038138

[51] Int. Cl.$^4$ .......................... C07C 45/34
[52] U.S. Cl. .............................. 568/401
[58] Field of Search ......................... 568/401

[56] References Cited

U.S. PATENT DOCUMENTS 3,932,521  1/1976  Gloyer et al. ............ 568/401
4,085,145  4/1978  Mimoun et al. ........... 568/401

FOREIGN PATENT DOCUMENTS 2744207  4/1978  Fed. Rep. of Germany ...... 568/401

OTHER PUBLICATIONS

Mimoun et al, J.A.C.S., vol. 100, pp. 5437–5443, (1978).
Raushel et al, J.A.C.S., vol. 102, pp. 6616–6619, (1980).
Davies et al, Chem. Abst., vol. 90, #202,999b, (1979).
Boschi et al, Chem. Abst., vol. 91, #57169v, (1979).

*Primary Examiner*—James H. Reamer
*Attorney, Agent, or Firm*—Beall Law Offices

[57] ABSTRACT

A process for producing methyl ethyl ketone selectively and with a high yield by oxygen-oxidizing 1-butene under mild conditions is provided, which process is characterized by using a composite catalyst containing a complex ($M_mX_n.L_l$) capable of forming an oxygen complex by coordination of the complex with oxygen and a complex catalyst ($M'_{m'}X'_{n'}.L'_{l'}$) capable of forming a 1-butene complex by coordination of the complex with 1-butene, wherein M represents a specified transition metal such as Cu; X, an anion; L, an organic phosphorus compound as ligand; M', a specified transition metal such as palladium; L', a nitrile, organic fluorine or phosphorus compound as ligand; m, m', n and n', each a number determined by the valences of the transition metals and the anion; l and l', each the number of ligands.

14 Claims, 2 Drawing Figures

PROCESS FOR PRODUCING METHYL ETHYL KETONE

BACKGROUND OF THE INVENTION

1. Field of the Invention

This invention relates to a process for producing methyl ethyl ketone and more particularly it relates to a process for producing methyl ethyl ketone by oxidizing 1-butene by means of an oxygen complex.

2. Description of the Prior Art

Methyl ethyl ketone (hereinafter referred to often as MEK) is used as the solvent for nitrocellulose, acetylcellulose, etc. and also used in the process for dewaxing lubricating oils and further used as a raw material for methyl ethyl ketone peroxide which has been produced in a large amount as a curing agent for unsaturated polyester resins and as a polymerization initiator; thus MEK is an important intermediate product in chemical industries.

Heretofore the process for producing MEK is roughly classified into (1) a sec-butanol dehydrogenation process and (2) a n-butane oxidation process. In the dehydrogenation process, MEK is produced according a two-stage process wherein n-butene is prepared from n-butene, which is then dehydrogenated at 430°–450° C. and 3 atm by means of a Zn-Cu catalyst, and the yield of MEK is 80%. On the other hand, the n-butane oxidation process wherein acetic acid is produced at the same time includes a non-catalyst type oxidation process and a process by means of cobalt acetate. It has been regarded that according to the former, the reaction is carried out at 15–20 atm and 180° C. using a liquid primary oxidation product as solvent and the yield of MEK is 13%, while according to the latter, the reaction is carried out at 54 atm and 175° C. and the yield of MEK is 17% (see K. Werssemel & H. J. Arpe, Industrial Organic Chemistry, translated by T. Mukaiyama, PP. 165 and 266, Tokyo Kagaku Dojin (1978)). Since the processes are both carried out under conditions of relatively high temperatures and pressures and hence the amount of by-products is large, the selectivity of the reaction and the improvement in yield have raised a problem. Further, when excess dissolved oxygen is released into the gas phase part of the reactor, it mixes with butane, MEK and the like gas to have a possibility of troubles such as explosion whereby a countermeasure thereto is required (see Revised Complete Production Flow Sheet, edited by Kihara et al, Vol. II, page 286, Kagakukogyosha (1978)). Thus, it has a great meaning that MEK can be produced from 1-butene selectively even at a single step.

Further, as a process for oxidizing a terminal olefin utilizing the oxidative force of palladium chloride (Pd(2)Cl$_2$), Wacker process has been well known. According to this process, a redox system aqueous solution of Pd(2)/Pd(0) and Cu(2)/Cu(1) is employed and propylene oxidation is relatively easy, but in the case of 1-butene and higher olefins of 5 or more carbon atoms, since these olefins are hardly soluble in water, the reaction rate is notably retarded (see J. Tsuji, Catalyst, 25, 452 (1983)); hence it has been regarded that the production of MEK according to 1-butene oxidation by means of the oxidative force of Pd(2)Cl$_2$ has not been practically carried out (see T. Tamura, Catalyst, 21, 167 (1979)).

On the other hand, as to the oxygen complexes which function as an effective oxidizing agent for the oxidization reactions of organic substances, various studies have been made as a modeling of the respiratory reaction of living bodies (see H. Tsuchida, Introduction to Chemistry, No. 20, PP. 30–40 (1978)). Their examples are iron-heme protein in mammals and copper-heme protein in molluscs. In these proteins, the oxidative state of iron or copper is a lower valence state.

Usually, in the case of metal ions capable of taking various valences, lower valence ions turn to higher metal ions when they are contacted with oxygen as shown in the following equation:

$$Cu(1) + \tfrac{1}{4}O_2 + \tfrac{1}{2}H_2O \rightarrow Cu(2) + OH^- \qquad (1)$$

$$Fe(2) + \tfrac{1}{4}O_2 + \tfrac{1}{2}H_2O \rightarrow Fe(3) + OH^- \qquad (2)$$

However, in hemoglobin and hemocyanin, even when Fe(2) and Cu(1) are contacted with oxygen, the metal ions are not oxidized, but oxygen is coordinated with the metal ions in the form of oxygen molecule, that is, an oxygen complex is formed, which is stably existent.

The thus combined oxygen molecule is activated through its coordination with the metal ions to oxidize many organic substances at as low temperatures as the body temperatures of living bodies, and the reaction heat constitutes the energy source of living bodies. However, when such protein complexes are separated from living bodies, they are so unstable that the metal ions are readily oxygen-oxidized; hence the complexes cannot be a practical oxidizing agent. Thus, it has been earnestly desired in respect of application to a commercial oxidation reaction to use an artificial compound as an oxidizing agent and to find a complex capable of forming a stable oxygen complex by combining the compound with a suitable transition metal.

The object of the present invention is to provide, in view of the above prior art, a process for producing methyl ethyl ketone wherein 1-butene is subjected to oxygen-oxidation under mild conditions whereby MEK can be produced selectively and with a high yield.

SUMMARY OF THE INVENTION

In short, the present invention is directed to a process wherein there is used a composite catalyst containing as at least one component, a transition metal complex capable of forming an oxygen complex by coordination of oxygen molecule with the transition metal of the transition metal complex, and as another component, a transition metal complex capable of forming a 1-butene complex by coordination of 1-butene with the transition metal of the transition metal complex, and 1-butene activated by the complex formation is oxidized by the combined oxygen activated by the complex formation, to produce MEK under mild conditions in a non-aqueous solvent system.

Namely, the present invention resides in a process for producing methyl ethyl ketone by oxygen-oxidizing 1-butene in the presence of a metal complex catalyst, which process comprises using as the metal complex catalyst, a composite catalyst containing a complex MmXn.Ll) capable of forming an oxygen complex by coordination of the complex with oxygen and a complex (M'm'Xn'.L'l') capable of forming a 1-butene complex by coordination of the complex catalyst with 1-butene, wherein M represents a transition metal belonging to the group I, the groups IV to VII or iron group of the group VIII of the Periodic Table; X, an anion such as halogens; L, an organic phosphorus compound as a ligand; M', a transition metal belonging to platinum group of the group VIII of the Periodic Table; L', a nitrile, an organic fluorine compound or an organic phosphorus compound; m, m', n and n', each a number determined by the valences of the above transition metals and anion; and l and l', each the number of ligand.

The above m, m', n, n', l and l' each represent an integer in the range of 1 to 4.

DETAILED DESCRIPTION OF THE INVENTION

The present inventors have made extensive research on the oxygen complex functioning as an oxidizing agent which effectively functions for the 1-butene oxidation reaction, and as a result have found that as a representative example thereof, a complex of cuprous chloride (hereinafter referred to as CuCl(1)) with tris (dimethylamino) phosphine oxide (other name: hexamethylphosphoramide; hereinafter referred to as hmpa) which is a phosphoric acid derivative can form a stable oxygen complex, and also a complex of palladium chloride (hereinafter referred to as $Pd(2)Cl_2$) with acetonitrile (hereinafter referred to as $CH_3CN$) also can form a stable 1-butene complex. Further, we have found that the combined oxygen in the above oxygen complex functions as an effective oxidizing agent for the thus coordinated and activated 1-butene, to produce MEK under a mild condition of normal pressures, selectively and with a high yield.

The situation in which the present invention has been led and its principle will be described in more detail. The solution of monovalent copper compounds (e.g. Cu(1)Cl) has a specific feature of absorbing CO through coordination of CO with Cu(1). However, since Cu(1) compounds are difficultly soluble, it has been difficult to make the concentration of their solution higher.

The present inventors added Cu(1)Cl to liquid hmpa (m.p. 7° C., b.p. 230° C./760 mmHg) to form the following complex:

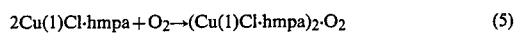

whereby we could make the concentration of the solution of Cu(1)Cl higher, and proposed an absorbing solution improved notably in the amount of CO absorbed and a process for separating and concentrating CO by the use of the solution (Japanese patent application laid-open Nos. Sho 56-118720 (1981) and Sho 57-19013 (1982)). The present complex can be expressed by the general formula MmXn.Ll. The above Cu(1)Cl.hmpa corresponds to the case where m=1, n=1 and l=1. Further, for example, if the central metal is Ti(3) or V(3), and the negative ion is Cl−, the resulting complex is $Ti(3)Cl_3$.hmpa or $V(3)Cl_3$.hmpa where m=1, n=3 and l=1.

Now, the solution of this Cu(1)Cl.hmpa which is a CO-absorbing solution also absorbs oxygen as well as CO and exhibits a deep green color. Usually when the solution of Cu(1) compounds absorbs oxygen, monovalent copper in a lower valency state is oxygen-oxidized into divalent copper in a higher valency state; hence the present inventors initially considered that a similar oxidation reaction might occur also in the Cu(1)Cl hmpa solution and as a result the color changed to green color.

Figure 1:
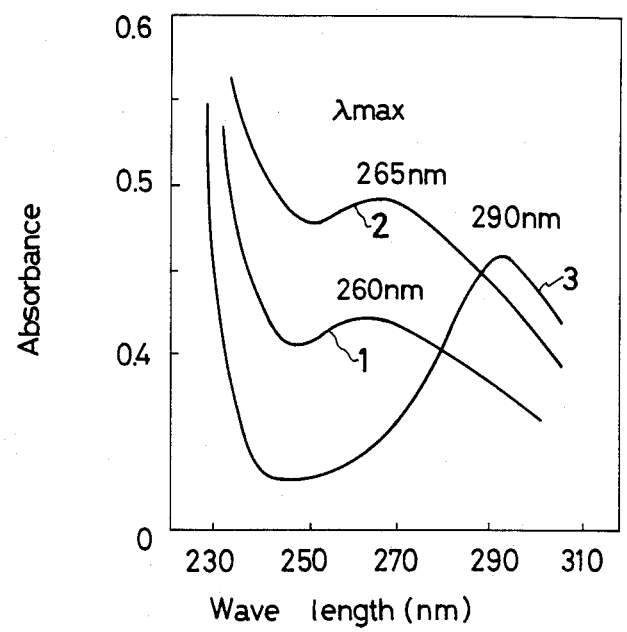
FIG. 1 shows the ultraviolet absorption spectra of the complexes related to the present invention.

However, the complex solution of the divalent copper compound ($Cu(2)Cl_2$) and hmpa exhibits a redbrown color. On the other hand, as to the colorless Cu(1).hmpa solution and a green color solution obtained by passing oxygen through the above solution to have oxygen absorbed therein, the respective ethyl alcohol solutions of the above solutions were subjected to measurement of their ultraviolet absorption spectra. The results are shown in FIG. 1. The spectra of the Cu(1) complex solution 1 and the complex solution 2 obtained by having oxygen absorbed in the former solution are entirely different from the spectra of the Cu(2) complex solution 3, and the complex compound solution 2 having oxygen absorbed therein and exhibiting a green color has a maximum absorption at 265 nm, which evidences formation of the so-called oxygen complex wherein oxygen molecule is coordinated. Thus, with a solution of Cu(1)Cl.hmpa complex having a definite concentration, the amount of oxygen absorbed was measured. As a result, it was found that the molar ratio of absorbed oxygen to Cu(1) was 1:2 and the compound having a maximum absorption at 265 nm and exhibiting a green color was an oxygen complex formed according to the following equation, and such an oxygen complex has never been reported:

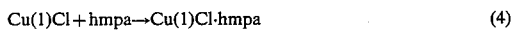

Namely, in the case of the Cu(1)Cl.hmpa solution, even when it absorbs oxygen, this oxygen is not consumed for oxidizing Cu(1) in the solution into Cu(2), but existent in the form of the so-called oxygen complex wherein oxygen molucle is coordinated with Cu(1). The specific feature of this oxygen complex is that the coordinated oxygen is not eliminated from the complex even when it is heated so that the absorption is irreversible. Thus, after the oxygen complex has been formed by contacting the above complex solution with oxygen or air, it is possible to easily remove excess free oxygen and also avoid troubles such as explosion due to direct mixing of oxygen with 1-butene at the gas phase part of the reactor. Further, the above oxygen complex is so stable that it requires even boiling at 100° C. e.g. for oxidation of Cu(1) into Cu(2) by means of the combined oxygen. Further, since the complex selectively absorbs oxygen from air to form all the same oxygen complex as that by means of pure oxygen, air is sufficient as the oxygen source in the reaction.

When a small molecule such as an oxygen is coordinated with a metal ion, the substrate is polarized and activated through electron transfer, and in the case of the above oxygen complex, too, found by the present inventors, the coordinated oxygen, of course, is activated. Further, in the case of the Cu(1)Cl.hmpa solution, the concentration of Cu(1)Cl therein can be easily raised up to 2 mols/l or more, and for example, when the cncentration is one mol/l, it is possible to dissolve 10 l or more of oxygen in one liter of the solution.

As described above, MEK is produced by oxidizing 1-butene by means of the combined oxygen activated by forming the oxygen complex, and if 1-butene can also be activated by forming a 1-butene complex, it will be possible to carry out the present oxidation reaction at lower temperatures and lower pressures. Thus, studies have been made on various complexes of transition metals of platinum group. In a representative example, palladium chloride (hereinafter referred to as Pd(2)Cl$_2$) formed a complex with the above hmpa (Pd(2)Cl$_2$.(hmpa)$_2$) and dissolved well in various solvents, but when 1-butene was passed through the complex, 1-butene complex was scarcely formed at atmospheric conditions. (However, 1-butene complex could be formed at least under the conditions of lower pressure and lower temperature than the prior art, such as 3 ata at 40° C.)

Thus, various studies have been made on a complex capable of forming a more stable 1-butene complex. The results will be described referring to the following representative example: When a nitrile such as acetonitrile (CH$_3$CN) was added as a modifying ligand (an auxiliary complexing agent), the following novel complex was formed:

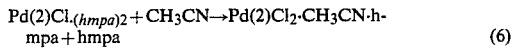

$$Pd(2)Cl_{(hmpa)2} + CH_3CN \rightarrow Pd(2)Cl_2 \cdot CH_3CN \cdot hmpa + hmpa \quad (6)$$

This complex is expressed by the general formula $M'm'Xn'.Ll'$, where $m'=1$, $n'=2$ and $l'=2$.

Figure 2:
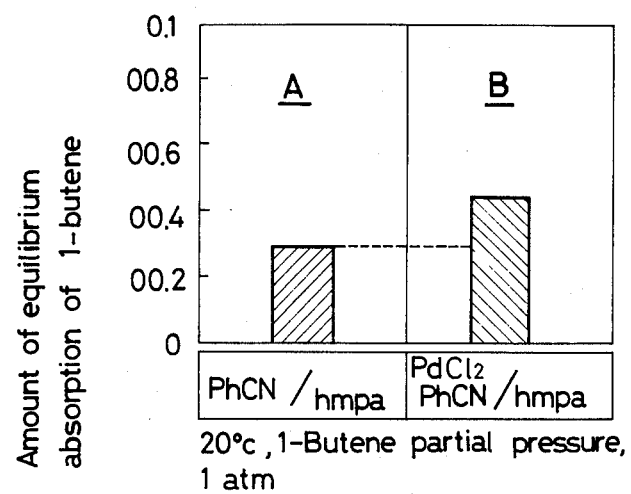
FIG. 2 shows a view illustrating that in view of the respective changes in the amount of 1-butene absorbed in a PhCN/hmpa solvent system and a $PdCl_2$/PhCN/hmpa system a 1-butene complex was formed in the latter system.

As to the formation of such a novel complex between the Pd(2) complex and 1-butene, studies were made according to gas absorption method. The results are shown in FIG. 2. When the case (A) of a solvent alone consisting of hmpa and benzonitrile (PhCN) was compared with the case (B) where Pd(2) complex was further present, the amount of 1-butene absorbed in the case B was about 1.6 times the amount in the case (A). Although the amount of 1-butene absorbed is large even in the case of the solvent alone due to the non-solvent system, the above difference in the absorption amount indicates that a novel 1-butene complex expressed by the following equation was formed:

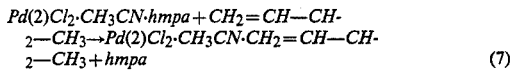

$$Pd(2)Cl_2 \cdot CH_3CN \cdot hmpa + CH_2=CH-CH_2-CH_3 \rightarrow Pd(2)Cl_2 \cdot CH_3CN \cdot CH_2=CH-CH_2-CH_3 + hmpa \quad (7)$$

Thus the formed 1-butene complex contains a notably activated 1-butene.

In short, when a binary system complex of Cu(1)Cl.hmpa and Pd(2)Cl$_2$.PhCN.hmpa is dissolved in a solvent such as hmpa, PhCN or sulfolane which function as a complexing agent at the same time, followed by passing air or pure oxygen through the resulting solution so as to give an adequate oxygen complex concentration, as described above, removing excess free oxygen by means of heating, degassing or the like if necessary, and passing 1-butene as a reaction substrate through the resulting solution to form an activated 1-butene complex, then this activated 1-butene is oxidized by the combined oxygen in the oxygen complex to quantitatively form MEK, as described later in Examples. This oxidation reaction is expressed by the following equation:

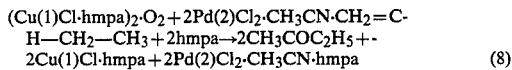

$$(Cu(1)Cl \cdot hmpa)_2 \cdot O_2 + 2Pd(2)Cl_2 \cdot CH_3CN \cdot CH_2=CH-CH_2-CH_3 + 2hmpa \rightarrow 2CH_3COC_2H_5 + 2Cu(1)Cl \cdot hmpa + 2Pd(2)Cl_2 \cdot CH_3CN \cdot hmpa \quad (8)$$

In such a manner, 1-butene coordinated with Pd(2) is oxidized by the oxygen molecule coordinated with Cu(1) complex. Thus, the valences of the metal ions in the complexes are unchanged, and also H$_2$O does not participate in the formation reaction of MEK. Even in this respect, the present production process is entirely different from the prior art wherein oxidation by way of the metal ion (Pd(2)) and H$_2$O is applied. As to the complex used, when the product is separated and thereafter air or oxygen is passed through the resulting catalyst solution, the oxygen complex is again formed, whereby it is possible to reuse the complex as the 1-butene oxidation catalyst. In addition, in the present invention, it does not matter if water is present in an amount in the range where no precipitate is formed.

In the present invention, since 1-butene is activated in the form of its complex, as described above, it is possible to produce MEK under mild conditions of e.g. the atmospheric pressure and 80° C. or lower, with a high selectivity and a high yield. And since MEK can be produced according to even a single stage process, it is possible to reduce the apparatus cost and utilities to a large extent as compared with the prior art.

In the composite catalyst system of the present invention, as M in MmXn.Ll as the complex catalyst capable of forming the oxygen complex, transition metals of Cu and Ag of the group I, Ti and Zr of the group IV, V and Nb of the group V, Cr, Mo and W of the group VI, Mn of the group VII and Fe, Co and Ni of the group VIII, each of the Periodic Table are preferable, and Cu(1), Ti(3) and V(3) are more preferable. Further, as X, halogens such as Cl$^-$, Br$^-$ and I$^-$ and anions such as BF$_4^-$, PF$_6^-$, SO$_3^{2-}$ and CH$_3$COO$^-$ are preferable and Cl$^-$, Br$^-$ and I$^-$ are more preferable. As the ligand L, phosphorous acid derivatives such as mono-, di- or triesters formed from reaction of phosphorous acid and methanol, ethanol, etc. and phenylphosphinous acid esters, dimethylphosphinic acid esters, triethylphosphine, triphenylphosphine, etc. and further phosphoric acid derivatives such as triphenylphosphine oxide, hexamethylphosphoramide and mono-, di- and triesters formed by reaction of phosphoric acid and methanol, ethanol, etc., and further organic phosphorus compounds represented by dimethyl methylphosphonate and methyl dimethylphosphinate are preferable, and hexamethylphosphoramide (hmpa) is particularly preferable.

On the other hand, as M' in the complex catalyst (M'm'Xn'.Ll') capable of forming 1-butene complex, lower valence ions among transition metals belonging to platinum group of the group VIII of the Periodic Table are preferable, and Pd and Pt are particularly preferable. Further, as the ligand L', nitriles such as acetonitrile, propionitrile, benzonitrile, tolunitrile, etc. and the above organic phosphorus compounds and further organic fluorine compounds such as fluorinated toluene, benzotrifluoride, etc. are preferable, and among these, nitriles or mixtures of nitrile and hmpa are particularly preferable.

As a solvent used when the reaction of the present invention is carried out in solution state, those which dissolves the composite catalyst, and also is easily separated from the resulting MEK (b.p. 79.5° C./760 mmHg) and further reduces the viscosity of the catalyst solution to promote the material transfer are preferable, and at least one solvent selected from various solvents such as heptane, toluene, methylcyclohexane, methyl isobutyl ketone, cyclohexanone, ethanol, ethylene glycol, dioxane, ethylene carbonate, chlorobenzene, N-methylpyrrolidone, tetrahydrofuran, etc., or mixtures thereof are used, and further, when the ligand L or L' is liquid, it is also possible to use these as the solvent at the same time.

Further, in order to raise the selectivity and yield of the reaction, it is preferred to make coexistent a basic (electron-donating) compound such as sulfolane, dimethylsulfolane, dimethylsulfoxide, dimethylformamide, trimethylmethane, dimethylsulfone, water, etc. with the reaction system, as described later in Examples.

Further, in the present invention, it is also possible to have the composite complex supported on a porous carrier such as active carbon, silicates, porous glass, and further polymers having a macro-reticular structure, etc. to produce MEK by means of oxygen-oxidation of 1-butene.

A novel complex forming the oxygen-complex and the 1-butene complex and its specific features and further examples of production reactions using the same have been described above. The present invention will be described in more detail by way of Examples.

EXAMPLE 1

Into a 500 ml capacity test tube with ground stopper were fed cuprous chloride (hereinafter referred to as Cu(1)Cl) (5 g, 50 mmols) and hmpa (340 g) to prepare a Cu(1)Cl.hmpa complex solution (330 ml). Further, into another 500 ml test tube with ground stopper were fed palladium chloride (hereinafter referred to as Pd(2)Cl$_2$) (1.3 g, 7 mmols) and benzonitrile (hereinafter referred to as PhCN) (170 g) to prepare a Pd(2)Cl$_2$.PhCN complex solution (170 ml). Both the solutions were then transferred into a 1 l capacity reactor to prepare a catalyst solution (500 ml) containing 0.1 mol/l of Cu(1)Cl and 0.015 mol/l of Pd(2)Cl$_2$. Through this solution was passed oxygen (1,000 ml) at 25° C. under the atmospheric pressure. Oxygen (430 ml, 19 mmols) was absorbed to obtain a solution having an oxygen complex concentration of 0.038 mol/l. Nitrogen gas was then passed. As a result, only the remaining oxygen in the gas phase part of the reactor and the physically dissolved oxygen were removed, but elimination of the combined oxygen from the oxygen complex in the solution was not observed. After this operation, 1-butene (1,000 ml) was passed at 25° C. under the atmospheric pressure. 1-butene (550 ml, 25 mmols) was absorbed to give a 1-butene concentration in the solution of 0.045 mol/l. Just thereafter the solution was heated to 60° C., followed by reacting for one hour and two hours, cooling the reaction solution and analyzing the resulting product according to gas chromatography. As a result it was found that MEK was formed in 0.6 g (8 mmols) after one hour and in 0.8 g (11 mols) after 2 hours. The reaction of the oxygen complex with the 1-butene complex is carried out according to the above equation (8) and in this Example, the 1-butene complex is present in excess of the oxygen complex and hence the amount of MEK formed is regulated by the concentration of the oxygen complex. Thus, when the conversion of 1-butene in this Example is expressed on the basis of the concentration of the oxygen complex, it is 20% after one hour and 30% after 2 hours.

EXAMPLE 2

Reaction was carried out in the same manner as in Example 1 except that the reaction temperature was 80° C. As a result, MEK was formed in 2.2 g (31 mmols) after one hour and in 2.5 g (35 mmols) after 2 hours, and the yield of MEK was 82 % and 90 % based on the oxygen complex. In addition, as the reaction temperature is elevated, the oxidation rate of 1-butene becomes higher, but the solubility lowers; hence the concentration of 1-butene in the solution lowers and the MEK yield decreases. However, it is possible to keep the concentration of 1-butene in the solution constant even when the temperature is raised.

EXAMPLE 3

Reaction was carried out in the same manner as in Example 2 except that the amount of hmpa was 212 g and sulfolane was added in an amount of 961 g (8.0 mols). As a result, the yield of MEK was 92% after one hour and 98% after 2 hours. Thus, addition of a basic sulvent, sulfolane increased the MEK yield.

EXAMPLE 4

Example 3 was repeated except that Cu(1)Cl was replaced by Ti(3)Cl$_3$ (15.7 g, 0.1 mol), to form an oxygen complex (36 mmols/l). The yield based the oxygen complex after one hour was 34% and that after 2 hours was 40%.

EXAMPLE 5

Example 4 was repeated except that Ti(3)Cl was replaced by V(3)Cl$_3$ (15.7 g, 0.1 mol), to form an oxygen complex (7 mmols/l). The yield based on the oxygen complex after one hour was 52% and that after 2 hours was 59%.

EXAMPLE 6

Example 4 was repeated except that Pd(2)Cl$_2$ was replaced by Pt(2)Cl$_2$ (7.98 g, 0.03 mol). As a result, the yield of MEK based on the oxygen complex was 45% after one hour and 52% after 2 hours. The same procedure was also carried out in Example 5. As a result, the yield was 63% after one hour and 70% after 2 hours.

EXAMPLE 7

Example 3 was repeated except that Pd(2)Cl$_2$ was replaced by Pt(2)Cl$_2$ (7.98 g, 0.03 mol). As a result, the yield of MEK was 96% after one hour and 98% after 2 hours.

EXAMPLE 8

Reaction was carried out under the same conditions as in Example 3 except that Cu(1)Cl was replaced by cuprous bromide (Cu(1)Br). The yield of MEK was 94%.

EXAMPLE 9

Reaction was carried out under the same conditions as in Example 3 except that Cu(1)Cl was replaced by cuprous iodide (Cu(1)I). As a result, the yield of MEK was 96%.

EXAMPLE 10

Reaction was carried out under the same conditions as in Example 1 except that benzonitrile was replaced by propionitrile. The yield after 2 hours was 21%. Further, when the nitrile was replaced by acetonitrile, the yield was almost the same as above.

EXAMPLE 11

The same operation as in Example 3 was carried out except that benzonitrile was replaced by benzotrifluoride. The yield was 92%.

EXAMPLE 12

Beads of a macro-reticular type styrene-divinylbenzene copolymer (particle diameter, about 1 mm$\phi$; specific surface area, 700-800 m$^2$/g; Amberlite XAD-4 (trademark, manufactured by Organo Co.) (50 ml) were impregnated with a catalyst solution containing an oxygen complex of a composition shown in Example 3, followed by filtering by suction to prepare a particulate catalyst. This catalyst was filled in a hard glass reaction tube of 20 mm$\phi$ in inner diameter, followed by heating to 80° C., then passing 1-butene at a rate of 1 l/min (SV=1, 200 h$^{-1}$) and analyzing MEK in the exit gas. As a result, the resulting product was MEK, alone, and the yield based on the main component was 3% after the reaction started till the succeeding two hours. The exit gas was then recycled to seek the MEK yield based on the combined oxygen in the oxygen complex, which reached 85%. Further, 1-butene feed was once stopped, followed by passing air to regenerate the combined oxygen consumed by the reaction, and again carrying out the oxidation experiment under the above conditions, to obtain similar results.

From the foregoing, it became evident that even when the complex catalyst of the present invention was supported on a carrier, the oxidation reaction by way of the combined oxygen in the oxygen complex proceeded.

In addition, it was confirmed that as the carrier, porous carriers such as silicates, active carbon, porous glass, etc. were usable and as the treating method after the impregnation, methods such as passing of heated gas, lower temperature calcination, etc. were employable besides filtering by suction.

COMPARATIVE EXAMPLE 1

The same catalyst solution as in Examples 2 and 3, was prepared except that nitriles or organic fluorine compounds were not added, followed by the smae operation. As a result, any of the yields of MEK was 0.1% or less. From these results it was evidenced that nitriles and organic fluorine compounds as a modifying ligand changed the specific feature of the coordinated metal ion to form a stable 1-butene complex to thereby greatly contribute to the activation of 1-butene.

COMPARATIVE EXAMPLE 2

Into the same reactor as in Example 1 were fed Pd(2)Cl$_2$ (1.3 g) and hmpa (340 g) to prepare a hmpa solution of Pd(2)Cl$_2$.(hmpa)$_2$ complex. 1-butene was passed through the solution by the same operation as in Example 1 except that no oxygen was passed, followed by reaction under the same conditions (60° C., 2 hours) as in Example 1, but 1-butene was not oxidized at all. Further, no precipitate of metal palladium was formed. Thus, this evidences that oxidation by way of Pd(2) ion did not occur in a non-aqueous solvent of hmpa, etc.

COMPARATIVE EXAMPLE 3

Cu(1)Cl (5 g) was added to the complex solution prepared in Comparative example 2 to prepare a catalyst solution consisting of Cu(1)Cl/Pd(2)Cl$_2$/hmpa, followed by the same operation and reaction as in Comparative example 2, but oxidation of 1-butene was not observed at all. This evidenced that it was necessary to pass oxygen to thereby form an oxygen complex.

COMPARATIVE EXAMPLE 4

Benzonitrile was added to the complex solution prepared in Comparative example 3, followed by the same operation and reaction as in Comparative example 2. In this case, too, since no oxygen was passed, 1-butene oxidation was not observed.

COMPARATIVE EXAMPLE 5

Oxygen was passed as in Comparative example 2, but 1-butene did not reacted at all. This evidences that oxidation reaction of 1-butene by way of free oxygen does not occur in the instant reaction system. From the above Comparative examples 2 and 3, it is evidenced that the present invention is entirely different from the formation reaction of MEK from 1-butene by way of the Pd(2)Cl$_2$-Cu(2)Cl$_2$ redox system as catalyst. Further, oxygen was passed through the catalyst solution containing the 1-butene complex in Comparative example 4, to obtain MEK with almost the same yield as those in the above Examples.

From the foregoing it is evidenced that the present invention is a novel production process different from the prior art, wherein the combined 1-butene activated by forming a 1-butene complex is oxidized by the combined oxygen activated by forming an oxygen complex to produce MEK.

According to the present invention, 1-butene and oxygen are not directly contacted each in the form of free oxygen, but they are coordinated with transition metal ions in a specified composite catalyst system and reacted together each in an activated state; hence it is possible to carry out a highly efficient reaction at as low temperatures as those in the vicinity of room temperature, under the atmospheric pressure and with a high yield. Further, since the reaction is carried out under mild conditions, the amount of by-products is small and the production steps including subsequent purification are simplified. Furthermore, since oxygen is selectively absorbed even when air is used as the oxygen source, all the same effectiveness as in the case where pure oxygen is used is obtained. Still further, since the oxygen absorption is irreversible, it is possible to easily remove excess free oxygen after the oxygen complex has been formed; hence the present invention is very advantageous even in the aspect of safety.

What we claim is:

1. A process for producing a methylethylketone by oxidizing 1-butene in the presence of a metal complex, comprising:
    contacting a first metal catalyst M$_m$X$_n$.L$_l$ with oxygen to form an oxygen complex;
    contacting a second catalyst M'$_m$'X$_n$'.L'$_l$' with 1-butene to form a 1-butene complex; and
    contacting the oxygen complex with the 1-butene complex to produce methylethylketone, wherein M represents a transition metal selected from the group consisting of Group I, Groups IV-VII and the iron group of Group VIII of the Periodic Table; X, an anion; L, an organic phosphorous compound selected from the group consisting of phosphorous acid esters, phosphoric acid esters, phyenylphosphinous acid esters, dimethylphosphinic acid esters, triethylphosphine, triphenylphosphine, triphenylphosphine oxide, dimethyl methylphosphonate, methyl dimethylphosphonate and hexamethylphosphoramide; M', a transition metal selected from the platinum group of Group VIII of the Periodic Table; L', a ligand selected from the group consisting of at least one of acetonitrile, propionitrile, benzonitrile, tolunitrile, phosphorus acid esters, phosphoric acid esters, phenylphosphinous acid esters, dimethylphosphinic acid ester, triethylphosphine, triphenylphosphine, triphenylphosphine oxide, dimethyl methylphosphonate, methyl dimethylphosphonate, fluorinated toluene, benzotrifluoride, and hexamethylphosphoramide; m, $m^1$ and n, $n^1$, each a number determined by the valences of the above transition metals and anions, and l and l1, each the number of the ligand and each are an integer in the range of 1 to 4.

2. The process of claim 1 further comprising the steps of separating the first metal catalyst from the resultant methylethylketone; and contacting said so-separated first metal catalyst with oxygen to regenerate said catalyst whereby it can be used to produce methylethylketone.

3. A process for producing methyl ethyl ketone according to claim 1, wherein said X is at least one anion selected from the group consisting of $Cl^-$, $Br^-$, $I^-$, $BF_4^-$, $PF_6^-$, $SO_4^{2-}$ and $CH_3COO^-$.

4. A process for producing methyl ethyl ketone according to claim 1, wherein said organic phosphorus compounds as said ligand L' are at least one compound selected from the group consisting of alkoxy, alkyl and amide derivatives of phosphorous acid or phosphoric acid.

5. A process for producing methyl ethyl ketone according to claim 1, wherein as a solvent for said complex capable of forming an oxygen complex and said complex capable of forming a 1-butene complex, there is used at least one compound selected form the group consisting of aliphatic, alicyclic and aromatic hydrocarbons, oxygen-containing organic compounds, organic halogen compounds and nitrogen-containing compounds.

6. A process, for producing methyl ethyl ketone according to claim 1, wherein said ligands L and L' are ligand and used at the same time as a solvent for said complex capable of forming an oxygen complex and said complex capable of forming a 1-butene complex.

7. A process for producing methyl ethyl ketone according to claim 1, wherein an oxygen-containing gas and 1-butene are passed through a solution of said composite catalyst to form said oxygen complex and said 1-butene complex to thereby react the both together.

8. A process for producing methyl ethyl ketone according to claim 1, wherein a porous carrier is impregnated with a solution of said composite catalyst to have said catalyst supported on said carrier, and an oxygen-containing gas and 1-butene are passed through the thus supported catalyst to oxidize the 1-butene by means of the combined oxygen in said oxygen complex.

9. A process for producing methyl ethyl ketone according to claim 1, wherein at least one basic (electron-donating) compound selected from the group consisting of sulfolane, dimethylsulfolane, dimethylsulfoxide and dimethylformamide is added.

10. A process for producing methylethylketone according to claim 1, wherein the transition metal Ti, Zr of Group IV, V, Nb of Group V, Cr, Mo and W of Group VI, Mn of the Group VII and Fe of Group VIII of the Periodic Table.

11. A process for producing methyl ethyl ketone according to claim 10, wherein the transition metal is selected from the group consisting of Cu, Ti and V.

12. A process for producing methyl ethyl ketone according to claim 1, wherein the transition metal M' is selected from the group consisting of Pd and Pt.

13. A process for producing methyl ethyl ketone according to claim 1, wherein the ligand L' is nitrile.

14. A process for producing methyl ethyl ketone according to claim 1, wherein the organic phosphorus compound is hexamethylphosphoramide.

* * * * *